United States Patent
Restaino

(10) Patent No.: US 6,617,149 B2
(45) Date of Patent: *Sep. 9, 2003

(54) **METHOD FOR ISOLATION AND IDENTIFICATION OF *ESCHERICHIA COLI* 0157:H7 AND PLATING MEDIA FOR SAID PROCESS**

(75) Inventor: Lawrence Restaino, Elburn, IL (US)

(73) Assignee: R&F Laboratories, Inc., West Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/100,261

(22) Filed: Mar. 18, 2002

(65) Prior Publication Data

US 2002/0142366 A1 Oct. 3, 2002

Related U.S. Application Data

(63) Continuation of application No. 09/553,964, filed on Apr. 21, 2000, now abandoned, which is a continuation of application No. 09/178,019, filed on Oct. 23, 1998, now Pat. No. 6,087,156, which is a continuation of application No. 09/714,690, filed on Sep. 16, 1996, now abandoned.

(51) Int. Cl.$^7$ .............................. C12N 1/20; C12Q 1/04; C12Q 1/10; C12Q 1/06; C12M 1/00
(52) U.S. Cl. ..................... 435/252.8; 435/34; 435/38; 435/39; 435/40; 435/253.6; 435/287.9
(58) Field of Search ................. 435/34, 38–40, 435/252.8, 253.6, 287.9

(56) References Cited

U.S. PATENT DOCUMENTS

| | | | |
|---|---|---|---|
| 5,393,662 A | * | 2/1995 | Roth et al. ..................... 435/34 |
| 5,418,167 A | * | 5/1995 | Matner et al. ............... 435/288 |
| 5,541,082 A | * | 7/1996 | Botchner ..................... 435/34 |
| 6,087,156 A | * | 7/2000 | Restaino .................. 435/287.9 |

OTHER PUBLICATIONS

Weagant et al. J. Food Protect. vol. 58, No. 1, pp. 7–12.*
Padhye et al. J. Food Protect. vol. 55, No. 7, pp. 555–565.*
Okrend et al. J. Food Protect. vol. 53, No. 11, pp. 941–943.*

* cited by examiner

Primary Examiner—Christopher R. Tate
(74) Attorney, Agent, or Firm—Marshall A. Burmeister

(57) ABSTRACT

An isolation plating medium for use in processes for the presumptive identification of *Escherichia coli* 0157:H7 from a sample that also contains other strains of *Escherichia coli*. The plating medium comprises at least one carbohydrate that *Escherichia coli* 0157:H7 is incapable of fermenting, but other strains of *Escherichia coli* do ferment said carbohydrate, a pH indicator dye that changes the color of the plating medium to a first color when the pH of the medium changes, a chromogenic substrate that reacts to beta-galactosidase to form a precipitate in the plating medium of a second color which contrasts with the first color. Both *Escherichia coli* 0157:H7 and the other strains of *Escherichia coli* are beta-galactosidase producers during metabolism, whereby a microorganism which ferments the carbohydrate but does not produce beta-galactosidase will produce colonies in the plating medium of the first color, *Escherichia coli* 0157:H7 which does not ferment the carbohydrate but produces beta-galactosidase will produce colonies in the plating medium of the second color, and the other strains of *Escherichia coli* which ferment the carbohydrate medium and produce beta-galactosidase will produce colonies in the plating medium of a third color which is the color that results from the mixing of the first and second colors, and a sufficient mass of an agent to solidify the mixture. The invention also includes processes of using the plating medium to identify and enumerate *Escherichia coli* 0157:H7 and other microorganisms.

9 Claims, No Drawings

METHOD FOR ISOLATION AND IDENTIFICATION OF *ESCHERICHIA COLI* 0157:H7 AND PLATING MEDIA FOR SAID PROCESS

The present application is a continuation of application Ser. No. 09/553,964, filed Apr. 21, 2000, now abandoned, by Lawrence Restaino entitled METHOD FOR ISOLATION OF *ESCHERICHIA COLI* 0157:H7 AND PLATING MEDIA FOR SAID PROCESS, and application Ser. No. 09/553,964, is a continuation of application Ser. No. 09/178,019, filed Oct. 23, 1998, now U.S. Pat. No. 6,087,156, and application Ser. No. 09/178,019 is a continuation of application Ser. No. 08/714,690, filed Sep. 16, 1996 now abandoned. The present invention relates to a process for isolating *Escherichia coli* 0157:H7 from other strains of *Escherichia coli* and other microorganisms, and to a solid plating media suitable for use in that process.

BACKGROUND OF THE INVENTION

*Escherichia coli* 0157:H7 has been recognized as an important human pathogen. Studies have shown that it is principally transmitted through food, *Escherichia coli* 0157:H7: Epidemiology, Pathogenesis, and Methods for Detection in Food, Nisha V. Padhye and Michael P. Doyle—Journal of Food Protection, Vol. 55, No. 7, Pages 555–565 (July 1992). There is thus a need for a rapid diagnostic test for the presence of *Escherichia coli* 0157:H7 in food in order to prevent the spread of *Escherichia coli* 0157:H7 through the food supply.

Pradhye and Doyle, supra, survey methods of detection of *Escherichia coli* 0157:H7. A stable characteristic of *Escherichia coli* 0157:H7 is that it will not ferment sorbitol within 24 hours whereas other strains of *Escherichia coli* will produce fermentation in sorbitol under incubation temperatures within 24 hours, and this characteristic has been used in processes for the isolation of *Escherichia coli* 0157:H7 from other enterics. Since there are microorganisms other than *Escherichia coli* 0157:H7 that do not ferment sorbitol, including some strains of *Escherichia coli*, this characteristic is not sufficiently specific to serve as an identifying test for *Escherichia coli* 0157:H7.

Anita J. Okrend, Bonnie E. Rose and Charles P. Lattuada describe an improved plating medium in Use of 5-Bromo-4-Chloro-3-Indoxyl-Beta-D-Glucuronide in MacConkey Sorbitol Agar in the Isolation of *Escherichia coli* 0157:H7 from Ground Beef, Journal of Food Protection, Vol. 53, No.11, Pages 941–943 (November 1990). This article describes a plating medium in which 5-bromo-4-chloro-3-indoxyl-beta-D-glucuronide acid cyclohexylammonium salt was dissolved in ethanol and the solution added to MacConkey Sorbitol Agar. Since approximately 97% of all *Escherichia coli* are beta-glucuronidase positive, but *Escherichia coli* 0157:H7 is beta-glucuronidase negative, this medium responds to the presence of *Escherichia coli* 0157:H7 by isolating white colonies rather than isolating blue colonies resulting from beta-glucuronidase positive microorganisms.

The process of isolating and detecting the presence of *Escherichia coli* 0157:H7 in a test sample by means of the processes described above, requires inoculation of the plating medium with the test sample, incubating the inoculated plating medium for a period of time, usually over night, and examining the surface of the plating medium to locate colonies of microorganisms in the incubated plating medium. Identification of *Escherichia coli* 0157:H7 is determined by the shape of the colony, size of the colony and color of the colony in the plating medium.

The color of the colony in the plating medium is a characteristic of the particular medium. U.S. Pat. No. 5,464,755 of Barry Bochner entitled Microbiological Medium and Method of Assay for Bacteria describes a plating medium adapted to produce colonies in three different colors. The examination of incubated plating media under a microscope is an exacting and time consuming task, and in the plating methods of the prior art, a positive response results in a presumptive identification of *Escherichia coli* 0157:H7 which must be verified by other testing methods. In short, an identification of *Escherichia coli* 0157:H7 cannot be made by prior art methods in less than about one day and at substantial expense due to the labor required to analyze the plating medium and the cost of the plating materials.

In an article published in the Journal of Microbiology—Volume 39 (1993) at pages 133–158, by P. M. Zadik, P. A. Chapman and C. A. Siddons, entitled Use of Tellurite for the Selection of Verocytotoxigenic *Escherichia coli* 0157:H7, experiments are described in which plating media containing mixtures of MacConkey sorbitol and potassium tellurite are subjected to mixed cultures of microorganisms. It was found that such plating media can be effective to reduce the growth of other strains of *Escherichia coli* than *Escherichia coli* 0157:H7 without materially affecting the growth of *Escherichia coli* 0157:H7. Further, such plating media were found to suppress the growth of other important enteric microorganisms, excepting Shigella.

STATEMENT OF INVENTION

It is an object of the present invention to provide a method of isolating and presumptively identifying *Escherichia coli* 0157:H7 which utilizes solid plating media and is more reliable than plating media methods known to the art, that is, makes a positive presumptive identification of *Escherichia coli* 0157:H7 and reduces the percentage of false positive determinations from that of prior art plating methods.

It is a further object of the present invention to provide a method of isolating and presumptively identifying *Escherichia coli* 0157:H7 which utilizes a solid plating medium and achieves its results in a significantly shorter time than processes of the prior art.

It is a further object of the present invention to provide a method of isolating and presumptively identifying *Escherichia coli* 0157:H7 which utilizes a solid plating medium and achieves its results at a significantly lower cost than processes of the prior art.

It is also an object of the present invention to provide plating media adapted for use in the methods described above.

The present invention comprises a solid plating medium which utilizes three mechanisms to produce an indication of the presence of *Escherichia coli* 0157:H7 in a test sample. First, the plating medium contains one or more carbohydrates which are not fermented by *Escherichia coli* 0157:H7 but may be fermented by other microorganisms including other strains of *Escherichia coli*. If a microorganism is present which ferments the carbohydrate, the medium is selected to change to a first color and indicates the presence of a microorganism other than *Escherichia coli* 0157:H7. Second, the plating medium contains a chromogen responsive to the presence of beta-galactosidase, and third, the plating medium contains ingredients for restricting the growth of microorganisms other than *Escherichia coli* 0157:H7.

More specifically, a solid plating medium for the presumptive identification of *Escherichia coli* 0157:H7 according to the present invention comprises: (1) at least one ingredient for differentiating *Escherichia coli* cells under incubation which is not fermented by *Escherichia coli* 0157:H7 but is fermented by other microorganisms including other strains of *Escherichia coli*, and if fermented results in a change in the pH of the medium; (2) a pH indicator dye which changes to a first color when the pH of the medium changes, (3) an ingredient for inhibiting the growth of gram positive microorganisms under incubation; (4) an ingredient for inhibiting the growth of Proteus sp. under incubation; (5) an ingredient for inhibiting the growth of strains of *Escherichia coli* other than *Escherichia coli* 0157:H7 under incubation; and (6) a chromogenic substrate that upon reacting to beta-galactosidase forms a second color that can contrast with the first color and combine with the first color to form a third color which contrasts with the first and second colors, however *Escherichia coli* 0157:H7 retains the second color.

The method of presumptive identification of *Escherichia coli* 0157:H7 according to the present invention comprises inoculating a mass of the plating medium described above with the sample under test, thereafter incubating the mass of inoculated plating medium at a temperature between 30 degrees and 40 degrees Celsius for a sufficient period of time to produce microorganism colonies in the mass of plating medium, and thereafter examining the surface of the mass of plating medium for colonies of the second color. Emergence of the first or the third color, which is a blend of the first and second colors, indicates the presence of microorganisms other than *Escherichia coli* 0157:H7.

The invention will be more readily understood from the following detailed description of the invention, which contains no drawing.

DETAILED DESCRIPTION OF THE INVENTION

The inventors' preferred detection system for *Escherichia coli* 0157:H7 utilizes a solid plating medium containing sorbitol, adonitol, salicin, inositol, indoxyl-beta-D-galactopyranoside and tellurite. Growth of microorganisms in this medium, specifically including *Escherichia coli* 0157:H7, can result in production of beta-galactosidase, which reacts with indoxyl-beta-D-galactopyranoside to produce an insoluble precipitate with a blue color. Hence, the presence of colonies of microorganisms that produce beta-galactosidase in the medium and do not produce acids from the carbohydrates, such as *Escherichia coli* 0157:H7, are blue and clearly visible and defined.

The presence of tellurite in the medium suppresses the growth of most microorganisms other than *Escherichia coli* 0157:H7, and a few others, that are suppressed by other means to be described hereinafter. Hence, the observance of blue with black percipitate colonies on the surface of the plating medium is a direct indication of *Escherichia coli* 0157:H7 and a presumptive identification.

While *Escherichia coli* 0157:H7 is sorbitol, adonitol, salicin and inositol negative, >99.0% of *Escherichia coli*, and most other enteric microorganisms, are positive for these carbohydrates. Microbial fermenting of sorbitol, adonitol, salicin and inositol changes the pH of the medium, thus producing colonies influenced by the indicator dye, i.e. yellow in the following examples. Hence, the presence of a yellow colony on the surface of an incubated plating medium of the present invention, is an indication of the presence of a microorganism other than *Escherichia coli* 0157:H7. Colonies produced by a microorganism which is both a sorbitol fermenter and beta-galactosidase positive are of a third color that is a blend of the first and second colors, namely green in the foregoing example, and most *Escherichia coli* other than *Escherichia coli* 0157:H7 are included in this group.

Sorbitol is the main carbohydrate ingredient of the plating medium. Other carbohydrates which are not fermented by *Escherichia coli* 0157:H7, but are by certain other strains of *Escherichia coli*, are salicin, inositol and adonitol, and these compositions and sorbitol, or a mixture thereof, have been found suitable for the carbohydrate ingredient of the plating media. Alternative carbohydrates at concentrations up to 10.0 grams per liter are mannitol, dulcitol, d-sorbitol, L-arabinose, L-rhamnose, d-xylose, trehalose, d-mannose, and melibiose.

Indoxyl-beta-D-galactopyranoside is a chromogen that reacts to the presence of beta-galactosidase. Beta-galactosidase is an enzyme produced by *Escherichia coli* and other coliforms, and this enzyme reacts with indoxyl-beta-D-galactopyranoside to produce an insoluble indigo blue precipitate. Other chromogens may be used in place of, or in combination with, indoxyl-beta-D-galactopyranoside, such as 5-bromo-4-chloro-3-indoxyl-beta-D-galactopyranoside.

In the preferred embodiment, isopropyl-beta-D-thiogalactopyranoside is also added to the plating medium. This ingredient enhances the production of the beta-galactosidase enzyme.

Also in the preferred embodiment of the present invention, other inhibitors which will not inhibit the growth of *Escherichia coli* 0157:H7 are employed in addition to tellurite. An inhibitor for gram positive bacteria is utilized, and in the preferred composition it is bile salts #3. Other inhibitors of gram positive bacteria can also be employed.

The medium of the preferred embodiment also contains a growth inhibitor for Proteus sp, namely, sodium novobiocin. Other inhibitors for Proteus sp. could also be employed.

The plating medium of the present invention also contains nutrients to promote the growth of microorganisms, especially protein. In the preferred embodiment, a mixture of tryptone, bacto-peptone and proteose-peptone is used, but it is to be understood that each of these ingredients can be separately used or used in combination with other nutrients. Further, there are many other nutrients which will support the growth of microorganisms that may be used in place of the above named nutrients.

The preferred embodiment also uses a pH indicator dye to permit ready determination of the pH of the medium. The pH of the medium is adjusted to 6.6 to 6.8. Sodium chloride is also added to the medium for osmolarity purposes.

There are some strains of *Escherichia coli*, including *Escherichia coli* 0157:H7, and some other microorganisms, that are not sorbitol fermenters, but are beta-glucuronidase active. Unless such microorganisms are beta-galactosidase producers, the medium described above is not responsive to such microorganisms, but is more specific to *Escherichia coli* 0157:H7. Optionally, a beta-glucuronidase chromogen may be admixed with the medium to produce a response to beta-glucuronidase. A preferred beta-glucuronidase chromogen is 6-chloro-3-indoxyl-beta-D-glucuronide that responds to beta-glucuronidase by producing a salmon precipitate in the plating medium that may be observed and counted.

The preferred embodiment of the plating medium contains the ingredients in the proportions set forth in the following Table I.

TABLE I

| MATERIAL | MEASUREMENT |
| --- | --- |
| Tryptone | 5.0 grams/liter |
| Bacto-peptone | 10.0 grams/liter |
| Proteose-peptone | 3.0 grams/liter |
| Sorbitol | 12.0 grams/liter |
| Salicin | 10.0 grams/liter |
| Inositol | 10.0 grams/liter |
| Adonitol | 8.0 grams/liter |
| Sodium chloride | 5.0 grams/liter |
| Phenol red | 0.1 grams/liter |
| Bile salts #3 | 1.25 grams/liter |
| indoxyl-beta-D-galactopyranoside | 0.120 grams/liter |
| 5-bromo-4-chloro-3-indoxyl-beta-D-galactopyranoside | 0.120 grams/liter |
| isopropyl-beta-D-thiogalactopyranoside | 0.100 grams/liter |
| Agar | 15 grams/liter |
| Novobiocin | 10 milligrams/liter |
| Potassium tellurite | 0.5 to 2.0 milligrams/liter |
| OPTIONAL | |
| 6-chloro-3-indoxyl-beta-D-glucuronide | 0.120 grams/liter |

Except for novobiocin and potassium tellurite, the 10 ingredients are mixed in any order, the pH adjusted to 6.6 to 6.8, boiled to sterilize the mixture, and the mixture is permitted to cool to room temperature. Thereafter, sterile novobiocin and sterile potassium tellurite at room temperature are added aseptically to the other ingredients. The composition is then poured into plates and permitted to dry for 48 to 72 hours, and it is then ready to be used. Storage time of poured plates is as much as 90 days at 2 to 8 degrees Celsius.

The process of the present invention requires a plate or mass of the plating medium to be inoculated with the test sample, and the inoculated mass is then incubated for a period of time to permit growth of the microorganisms in the test sample to observable colonies. The inventor has found that with the preferred plating medium described above, a period of 24 hours of incubation is sufficient time for *Escherichia coli* 0157:147 colonies present in raw hamburger to grow into colonies that are readily observable with a naked eye. It is believed that the abundant growth of microorganisms in the preferred plating medium is due to the nutrients provided by the tryptone, bacto-peptone, proteose-peptone, sorbitol, salicin, inositol and adonitol. The surface of the plating medium mass is then assayed and the presence and number of blue with black precipitate colonies recorded. Also, the presence of white or yellow to green colored colonies is noted as an indication of microorganisms other than *Escherichia coli* 0157:H7.

It is to be noted that no special equipment is required to observe the incubated mass of plating medium. The time required to note the number and presence of blue with black precipitate colonies is far less than required when other colonies are present. Also, there are no ingredients in the plating medium that are especially costly. Hence, an assay of a test sample may be made at reduced cost from assays with prior plating media.

The following Table II sets forth examples of use of the plating medium described in Table I, without the optional substrate, by the process described above, the test sample containing the microorganism shown in the left column and the observed colonial description being set forth in the right column.

TABLE II

| Bacterial species | # of Strains | Colonial Morphology |
| --- | --- | --- |
| *Escherichia coli* 0157:H7 Typical strains | 26 | Domed to raised colony; 1.5–2.5 mm in diameter. Dark blue to black color. No ring around colony. |
| *Escherichia coli* 0157:H7 Beta-glucuronidase positive | 1 | Domed to raised colony; 2.0 mm in diameter. Dark blue to black color. No ring around colony. |
| *Escherichia coli* 0157:H7 Sorbitol positive | 1 | Domed to raised colony; 2.0 mm in diameter. Blue to turquoise color. No ring around colony. |
| *Escherichia hermannii* | 2 | Domed; pinpoint to <1 mm in diameter; clear to light blue color |
| *Escherichia coli* | 9 | 3 strains no growth. Pinpoint to 2 mm in diameter; clear to green color. |
| *Salmonella* spp. | 5 | Minimal growth; <1 to 1 mm in diameter; clear/white to yellow color |
| *Pseudomonas cepacia* | 1 | Domed; 1 to 2 mm in diameter. Clear color. |
| *Pseudomonas aeruqinosa* | 2 | Domed; pinpoint to <1 mm in diameter. Clear color. |
| *Providencia stuartii* | 1 | Domed; <1 mm in diameter. Clear to white color. |
| *Pseudomonas picketti* *Klebsiella* spp *Enterobacter* spp. *Proteus* spp. *Morganella* sp. *Citrobacter* spp. *Acinetobacter calcoaceticus* *Providencia alcalifaciens* *Yersinia enterocolitica* | 16 | No growth for all strains |

Those skilled in the art will devise other methods of utilizing the plating media of the present invention, and other plating media than those specifically described in the foregoing specification within the scope of the present invention. It is therefore intended that the scope of the present invention be not limited by the foregoing specification, but rather only by the appended claims.

The invention claimed is:

1. An isolation plating medium for use in processes for the presumptive identification of *Escherichia coli* 0157:H7 from a test sample that also contains other bacteria including other strains of *Escherichia coil*, both Escherichia coil 0157:H7 and the other strains of *Escherichia coil* being beta-galactosidase producers during metabolism, comprising at least one carbohydrate that is a member of the group sorbitol, salicin, inositol, adonitol, mannitol, dulcitol, d-sorbitol, L-arabinose, L-rhamnose, d-xylose, trehalose, d-mannose, and melibiose, *Escherichia coil* 0157:H7 being incapable of fermenting said carbohydrate but other strains of *Escherichia coli* fermenting said carbohydrate, a pH indicator dye that changes the color of the plating medium to a first color when the pH of the medium changes, a chromogenic substrate that reacts to beta-galactosidase to form a precipitate in the plating medium of a second color which contrasts with the first color, whereby a microorganism which ferments the carbohydrate but does not produce beta-galactosidase will produce colonies in the plating medium of the first color, a microorganism which does not ferment the carbohydrate but produces beta-galactosidase including *Escherichia coli* 0157:H7 will produce colonies in the plating medium of the second color, and microorganisms which ferment the carbohydrate and produce beta-galactosidase including the other strains of *Escherichia coli* will produce colonies in the plating medium of a third color which is the color that results from the mixing of the first and second colors, and a sufficient mass of an agent to solidify the mixture.

2. An isolation plating medium according to claim 1 wherein the chromogenic substrate consists of one or more members of the group indoxyl-beta-D-galactopyranoside and 5-bromo-4-chloro-3-indoxyl-beta-D-galactopyranoside.

3. An isolation plating medium according to claim 1 wherein the plating medium further comprises a nutrient base consisting of one or more members of the group tryptone, bacto-peptone, and proteose-peptone.

4. An isolation plating medium according to claim 3 wherein the plating medium further comprises tellurite.

5. A method of detecting the presence of *Escherichia coli* 0157:H7 in a test sample that contains other bacterial strains including other *Escherichia coli* strains comprising the steps of inoculating a solid plating medium with said sample, wherein said plating medium comprises at least one carbohydrate that is a member of the group sorbitol, salicin, inositol, adonitol, mannitol, dulcitol, d-sorbitol, L-arabinose, L-rhamnose, d-xylose, trehalose, d-mannose, and melibiose, *Escherichia coli* 0157:H7 being incapable of fermenting said carbohydrate but other strains of *Escherichia coli* fermenting said carbohydrate, a pH indicator dye that changes the color of the plating medium to a first color when the pH of the medium changes, a chromogenic substrate that reacts to beta-galactosidase to form a precipitate in the plating medium of a second color which contrasts with the first color, whereby a microorganism which ferments the carbohydrate but does not produce beta-galactosidase will produce colonies in the plating medium of the first color, a microorganism which does not ferment the carbohydrate but produces beta-galactosidase including *Escherichia coli* 0157:H7 will produce colonies in the plating medium of the second color, and microorganisms which ferment the carbohydrate and produce beta-galactosidase including the other strains of *Escherichia coli* will produce colonies in the plating medium of a third color which is the color that results from the mixing of the first and second colors, and a sufficient mass of an agent to solidify the mixture, thereafter incubating said plating medium for a sufficient period to obtain colonies of bacterial strains producing one or more of said colors, and examining the plating medium for colonies of said first second and third colors.

6. A method of detecting the presence of *Escherichia coli* 0157:H7 according to claim 5 wherein the plating medium further comprises a nutrient base consisting of one or more members of the group tryptone, bacto-peptone, and proteose-peptone.

7. A method of detecting the presence of *Escherichia coli* 0157:H7 according to claim 5 wherein the plating medium further comprises tellurite.

8. An isolation plating medium according to claim 1 wherein the plating medium further comprises tellurite.

9. An isolation plating medium for use in processes for the presumptive identification of *Escherichia coli* 0157:H7 from a test sample that also contains other bacteria including other strains of *Escherichia coli*, both *Escherichia coli* 0157:H7 and the other strains of *Escherichia coli* being beta-galactosidase producers during metabolism, comprising a nutrient base consisting of one or more members of the group tryptone, bacto-peptone, and proteose-peptone, tellurite, at least one carbohydrate, said carbohydrate being a member of the group sorbitol, salicin, inositol, adonitol, mannitol, dulcitol, d-sorbitol, L-arabinose, L-rhamnose, d-xylose, trehalose, d-mannose, and melibiose, *Escherichia coli* 0157:H7 being incapable of fermenting said carbohydrate but other strains of *Escherichia coli* fermenting said carbohydrate, a pH indicator dye that changes the color of the plating medium to a first color when the pH of the medium changes, a chromogenic substrate that reacts to beta-galactosidase to form a precipitate in the plating medium of a second color which contrasts with the first color, said substrate being a member of the group indoxyl-beta-D-galactopyranoside and 5-bromo-4-chloro-3-indoxyl-beta-D-galactopyranoside, whereby a microorganism which ferments the carbohydrate but does not produce beta-galactosidase will produce colonies in the plating medium of the first color, a microorganism which does not ferment the carbohydrate but produces beta-galactosidase including *Escherichia coli* 0157:H7 will produce colonies in the plating medium of the second color, and microorganisms which ferment the carbohydrate and produce beta-galactosidase including the other strains of *Escherichia coli* will produce colonies in the plating medium of a third color which is the color that results from the mixing of the first and second colors, and a sufficient mass of an agent to solidify the mixture.

\* \* \* \* \*